United States Patent [19]

Nicholson et al.

[11]  4,304,931
[45]  Dec. 8, 1981

[54] BIPHENYLHYDROXYPROPIONIC ACID DERIVATIVES

[75] Inventors: John S. Nicholson, Beeston; John L. Turner, East Leake, both of England

[73] Assignee: The Boots Company Limited, Nottingham, England

[21] Appl. No.: 62,972

[22] Filed: Aug. 2, 1979

Related U.S. Application Data

[60] Division of Ser. No. 889,644, Mar. 24, 1978, Pat. No. 4,188,491, which is a continuation of Ser. No. 672,300, Mar. 31, 1976, abandoned.

[30] Foreign Application Priority Data

Apr. 4, 1975 [GB] United Kingdom ............... 13817/75

[51] Int. Cl.³ ............................................. C07C 59/01
[52] U.S. Cl. ................................................... 562/469
[58] Field of Search ................................ 562/492, 469

[56] References Cited

U.S. PATENT DOCUMENTS 3,624,142  11/1971  Shen ................................... 562/492

FOREIGN PATENT DOCUMENTS 2409761  11/1975  Fed. Rep. of Germany ...... 562/469
1091403  11/1967  United Kingdom ............... 562/469

Primary Examiner—Paul J. Killos
Attorney, Agent, or Firm—Gordon W. Hueschen

[57] ABSTRACT

A process is disclosed for preparing arylpropionic acids of formula Ar—CH(CH₃)—COOH, by reacting an aryl Grignard reagent with a metal pyruvate or with a pyruvamide, to form a hydroxy acid of formula Ar—C(OH)(CH₃)—COOH or its amide, and converting the acid or amide to the product.

1 Claim, No Drawings

BIPHENYLHYDROXYPROPIONIC ACID DERIVATIVES

This is a division of application Ser. No. 889,644, filed Mar. 24, 1978, U.S. Pat. No. 4,188,491 which is a continuation of application Ser. No. 672,300 filed Mar. 31, 1976, now abandoned.

This invention relates to therapeutic agents and in particular to a process for preparing therapeutic agents.

It is well known that a large number of 2-arylpropionic acids, and derivatives thereof have valuable therapeutic properties, and many possess, for example, anti-inflammatory activity. The present invention relates to a method of preparing such acids and to methods for preparing intermediates to these acids.

Various methods have been proposed for the preparation of 2-arylpropionic acids including processes which involve 2-aryl-2-hydroxypropionic acids or their derivatives, as intermediates. In such processes the 2-aryl-2-hydroxypropionic acids are converted to the desired 2-arylpropionic acid, in which the hydroxyl group is replaced by hydrogen, in various known ways. For example, 2-aryl-2-hydroxypropionic acids can be dehydrated to the corresponding 2-arylacrylic acids. These can then be hydrogenated to form the desired 2-arylpropionic acids. It is known that with some 2-arylpropionic acids, the majority or nearly all the therapeutic activity of one of the stereoisomers is greater than that of its enantiomer. If desired the 2-arylacrylic acid can be hydrogenated under conditions which will preferentially form one of the stereoisomers of the 2-arylpropionic acid in a greater proportion than its enantiomer. Thus, an effective route for the preparation of 2-aryl-2-hydroxypropionic acids is highly desirable.

In our B. Pat. No. 971,700 we disclose a process in which ethyl pyruvate is reacted with a Grignard reagent to give a 2-aryl-2-hydroxypropionic acid ester which is hydrolysed to the 2-aryl-2-hydroxypropionic acid. It has also been disclosed (Chemistry and Industry 1970, 159) that an arylmagnesium bromide can be reacted with pyruvic acid to give a 2-aryl-2-hydroxypropionic acid. However, the yields in these processes tend to be low. For instance, in two typical processes, the details of which are given below, the yields are 14.5 and 18%.

We have now found that when an arylmagnesium bromide is reacted with certain salts or with certain amides of pyruvic acid, the resultant addition product is obtained in a higher yield than when the arylmagnesium bromide is reacted with pyruvic acid or an ester thereof. For example, yields of over 70% of high quality 2-(2-fluoro-4-biphenylyl) propionic acid have been obtained by reacting sodium pyruvate with 2-fluoro-4-biphenylylmagnesium bromide.

Thus, according to the present invention, there is provided a process for preparing a compound of formula I, $$\text{Ar}-\overset{\text{CH}_3}{\underset{}{\text{CH}}}-\text{COOH} \qquad \text{I}$$

wherein Ar is an aryl group, which comprises reacting a Grignard compound obtained from Ar₁Br and magnesium, wherein Ar₁ is Ar or a group convertible to Ar on acidification, with a compound of formula II, $$\text{CH}_3-\text{CO}-\text{COZ} \qquad \text{II}$$

wherein Z is OM or NR₁R₂ wherein M is an alkali metal and R₁ and R₂ are the same or different alkyl, alkenyl, or aryl or together with the nitrogen atom to which they are attached form a 5 to 7 membered ring, and acidifying the mixture to give a compound of formula III

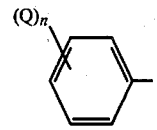

where Q is OH or NR₁R₂ and converting this, in known manner, to the compound of formula I.

The invention also includes the process of preparing the compounds of formula III as described above.

Generally Ar₁=Ar. The term "aryl" also includes heteroaryl e.g. thienyl, thiazolyl, pyrrolyl and triazinyl.

The Ar group is generally a substituted phenyl group of formula

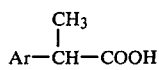

in which n is an integer of 1 to 4, preferably 1 or 2, and Q is the same or different and is selected from alkyl, preferably C₁₋₈ alkyl, e.g. methyl, ethyl, propyl, butyl, (especially isobutyl), pentyl, branched hexyl and heptyl; aralkyl, e.g. benzyl; cycloalkyl, e.g. of three to seven carbon atoms, and especially cyclohexyl; alkyl substituted cycloalkyl, e.g. monomethyl and monoethyl substituted cyclohexyl; aryl, e.g. phenyl and phenyl substituted with, for example 1 or 2 alkyl, preferably C₁₋₄ alkyl, alkoxy, preferably C₁₋₄ alkoxy, alkylthio, preferably C₁₋₄ alkylthio, especially methylthio, cyano or halogen, e.g. fluorine and chlorine; alkoxy preferably C₁₋₄ alkoxy, e.g. methoxy and isopropoxy; cycloalkoxy, e.g. cyclohexyloxy; aryloxy, e.g. phenoxy and phenoxy substituted with, for example 1 or 2 halogen atoms especially chlorine or fluorine; alkylthio, preferably C₁₋₄ alkylthio, e.g. methylthio, ethylthio, propylthio and n-butylthio; aralkylthio; cycloalkylthio; arylthio, e.g. phenylthio; arylcarbonyl, e.g. benzoyl and thenoyl; N-alkyl-N-arylamino in which the aryl is e.g. phenyl or phenyl substituted with, for example, one or more halogen atoms, especially fluorine or chlorine; N-alkyl-arylsulphonamido; trifluoromethyl; halogen, e.g. fluorine or chlorine; dialkylamino; pyridyl; piperidyl; furyl; morpholino; thiamorpholino; pyrrolidinyl; pyrrolyl; thienyl; or two Q groups together form a carbocyclic or heterocyclic ring, which rings may be aromatic, e.g. naphthyl and substituted naphthyl. When Q is a heterocyclic group it may be substituted or unsubstituted.

Examples of compounds are those in which the substituent or one of the substituents, Q, is in the 4-position, and is alkyl, e.g. isobutyl or cycloalkyl, e.g. cyclohexyl. Particularly preferred compounds are those in which Ar is

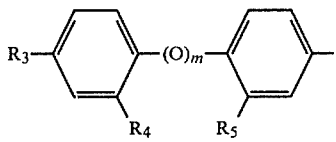

in which m is 0 or 1, and $R_3$, $R_4$ and $R_5$ may be the same or different and are selected from hydrogen, chlorine, fluorine or methoxy, at least one being chlorine, fluorine or methoxy and preferably fluorine. Especially preferred are those compounds in which m is 0.

Examples of such preferred Ar groups are the following;

| m | $R_3$ | $R_4$ | $R_5$ |
|---|---|---|---|
| 0 | H | F | H |
| 0 | H | H | F |
| 0 | H | F | F |
| 0 | F | F | H |
| 0 | F | H | F |
| 0 | F | F | F |
| 0 | F | H | H |
| 1 | F | H | H |
| 1 | F | F | H |
| 1 | H | F | H |
| 1 | F | Cl | H |
| 1 | Cl | H | H |
| 0 | H | H | OMe |
| 0 | Cl | F | F |
| 0 | F | F | Cl |
| 0 | F | Cl | F |
| 0 | Cl | H | H |

Other particularly suitable Ar groups include 2-(6-methoxy-2-naphthyl) and those in which n is 1 and Q is in the 3 position and is benzoyl or phenoxy.

$R_1$ and $R_2$ are for example lower alkyl, e.g. of 1 to 4 carbon atoms, and especially both methyl or both ethyl. Examples of suitable rings of which $R_1$ and $R_2$ can form part, include

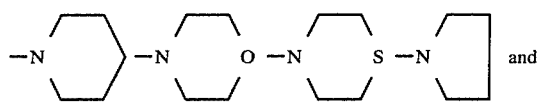 and

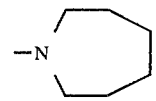

which rings may optionally carry one or more substituents, e.g. $C_{1-4}$ alkyl. When $R_1$ or $R_2$ is aryl, this is generally phenyl but it may also be substituted phenyl, e.g. tolyl. It is generally preferred, however, that in compound II, Z is OM, and M is preferably sodium. When a metal salt is used the method of its preparation may affect the yield of the 2-aryl-2-hydroxypropionic acid. If the salt forms a hydrate then it is preferable that it is prepared in a non-aqueous medium, preferably a $C_{1-4}$ alkanol, e.g. methanol. In the case of sodium pyruvate however, satisfactory results are obtained when the salt is prepared by reacting pyruvic acid with sodium carbonate in water, evaporating the solution and drying the residue in a vacuum.

The reaction for producing the compound of formula III is generally carried out in a conventional manner for Grignard reactions, e.g. in an anhydrous aprotic medium, preferably an ether, for example tetrahydrofuran, diethyl ether, 1,2-dimethoxyethane or a mixture of one or more of these. The reaction is generally carried out at a temperature of $-20°$ to $+150°$ C., preferably $-10°$ to $70°$ C. It may suitably be carried out under reflux.

When the acid of formula III is one in which the aryl group contains a functional group which is itself reactive with the Grignard compound e.g. a carbonyl group, it is usually necessary that this functional group be protected before the Grignard compound is formed. The protecting group is then removed on acidification. An example of a suitable carbonyl protecting group is a ketal, for example gem-dimethoxy.

As previously stated the compound of formula III can be converted to the compound of formula I in various known ways. The following scheme illustrates typical methods that can be applied.

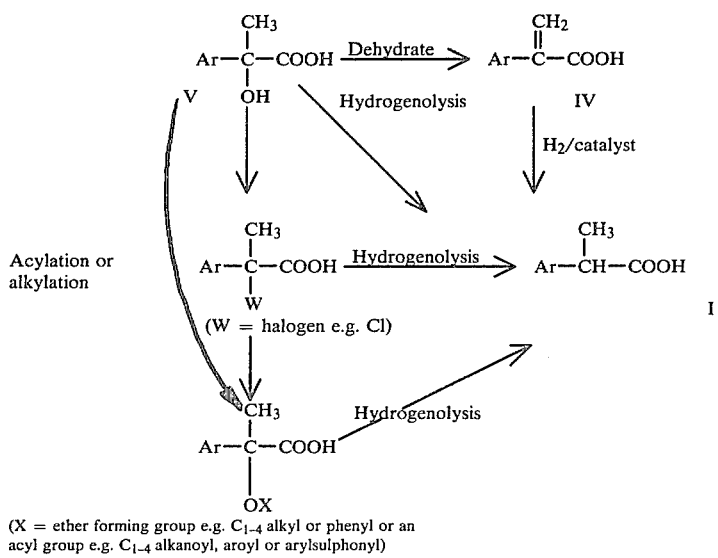

(X = ether forming group e.g. $C_{1-4}$ alkyl or phenyl or an acyl group e.g. $C_{1-4}$ alkanoyl, aroyl or arylsulphonyl)

In the above reactions it may be desirable to convert any of the acids to esters before proceeding to the next stage. The ester group is then eventually hydrolysed to give compound I.

If compound V is replaced by the corresponding amide the amide group can be hydrolysed to carboxyl at any suitable stage to obtain I.

The preferred method of converting III or V to I is by dehydration to IV followed by hydrogenation.

The dehydration reaction may be carried out merely by heating the compound of formula III or V. However, it is preferred to use a dehydrating agent e.g. polyphosphoric acid. Other dehydrating agents which may be used include formic acid; phosphorus pentoxide alone or mixed with methanesulphonic acid or a tertiary amine; iodine, mesyl chloride mixed with sulphur dioxide; toluene p-sulphonic acid; naphthalene β-sulphonic acid; phthalic anhydride mixed with propionic acid; potassium hydrogen sulphate; phosphoryl chloride in pyridine or dimethyl formamide; concentrated hydrochloric acid mixed with glacial acetic acid; propionic acid mixed with o-sulphobenzoic anhydride; and dimethyl sulphoxide. The dehydration may be carried out at a temperature for example of 0° C. to 300° C., preferably 0° C. to 200° C. and especially 80° C. to 150° C.

The hydrogenation of the compound of formula IV is generally carried out using a catalyst, e.g. palladium, usually on charcoal, platinum, ruthenium, Raney nickel or rhodium. The reaction is usually carried out in an inert solvent, e.g. a lower alkanol, benzene, toluene, xylene, tetrahydrofuran, dioxan, acetic acid or mixtures of two or more of these. The temperature of the hydrogenation may be, for example from 0° C. to 200° C.

If desired, the hydrogenation may be carried out using a catalyst which may form one of the stereoisomers in a greater proportion than its enantiomer. Such catalysts are usually complexes of transition metals with an organic compound having one or more asymmetric carbon atoms, for example, the reaction product of a Group VIII transition metal salt or a complex thereof and an optically active bidentate compound of formula:

$$(R)_2P—R'—P(R)_2$$

in which R' is a bivalent hydrocarbon group containing one or more asymmetric carbon atoms and optionally bearing one or more substituents, the asymmetric carbon atom(s) optionally forming part of a ring and each R is a substituted or unsubstituted aliphatic, cycloaliphatic or aromatic hydrocarbon radical. Examples of these catalysts are described in B. Pat. No. 1,341,857.

Generally this hydrogenation is carried out in the presence of a base usually an organic amine e.g. morpholine, aniline, isopropylamine, di-n-propylamine and tri-n-butylamine. A particularly suitable base is α-methylbenzylamine.

If a hydrogenolysis reaction is used this may be carried out using conditions similar to that of the hydrogenation including using catalysts to obtain a stereospecific reaction. However, it is not always necessary to use hydrogen and hydrogenolysis may sometimes be carried out, for example by heating the compound to be hydrogenolysed with a mixture of phosphorus and hydriodic acid.

If desired when the 2-aryl-2-hydroxypropionic acid is converted to the 2-arylpropionic acid, by means other than via the acrylic acid, then it may be possible to resolve this compound or, when going through an intermediate resolve the intermediate, by conventional means. The resolved products may then be hydrogenolysed to give the 2-arylpropionic acid in which one stereoisomer is present in a greater amount than its enantiomer.

As stated previously, compounds of formula I generally possess anti-inflammatory activity. Similarly, many compounds of formula III and IV also possess anti-inflammatory activity. Some of the compounds of formula III and IV are novel. Thus, the invention also provides compounds of formula

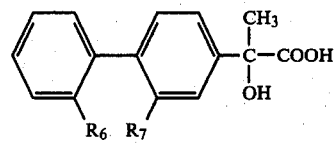

in which $R_6$ and $R_7$ are hydrogen or fluorine at least one being fluorine and especially 2-(2-fluoro-4-biphenylyl)-2-hydroxypropionic acid as well as enantiomers of these compounds. The invention also provides compounds of formula

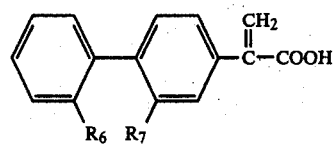

in which $R_6$ and $R_7$ are as defined above, and especially 2-(2-fluoro-4-biphenylyl)acrylic acid.

The invention is illustrated in the following Examples, in which "parts" and "percentages" are by weight, unless otherwise stated.

In the Examples "DIOP" is:

(−)-2,3-O-Isopropylidene-2,3-dihydroxy-1,4-bis-(diphenylphosphino)butane (J. Am. Chem. Soc. 1972,94,6429), DTDR is μ-dichlorotetracyclooctenedirhodium and DODDR is μ-dichlorodicycloocta-1,5-dionedirhodium. Optical rotations were determined in ethanol at a concentration of 1%.

EXAMPLE 1

A solution of 4-bromo-2-fluorobiphenyl (5 g., 0.02 mole) in dry tetrahydrofuran (20 ml.) was added dropwise, with stirring, to magnesium turnings (0.49 g.) in dry tetrahydrofuran (13 ml.). When the addition was complete, the mixture was stirred and boiled under reflux for one hour. A suspension of sodium pyruvate (2.2 g., 0.02 mole) in dry tetrahydrofuran (20 ml.) was added rapidly to the refluxing solution. Frothing occurred and when this had subsided the mixture was boiled under reflux with stirring for a further hour. The mixture was then cooled in an ice-bath and dilute hydrochloric acid (5 N; 50 ml.) was added. The mixture was stirred and extracted with ether. The extract was then extracted with aqueous potassium carbonate (1 N) and this extract acidified with dilute hydrochloric acid. The precipitate which separated, was collected and dried to give 2-(2-fluoro-4-biphenylyl)-2-hydroxypropionic acid, m.p. 166°-9° C. in 71% yield.

EXAMPLE 2

The product of Example 1 (2 g.) was mixed with polyphosphoric acid (10 g.) and heated at 100° C. for 30 minutes. Water was added and the mixture stirred and extracted with ether. The extract was dried, filtered and evaporated to give crude 2-(2-fluoro-4-biphenylyl)acrylic acid in a yield of 91%, m.p. 169°-172° C. This was recrystallised from a mixture of ether and light petroleum (b.p. 40°-60° C.) to give pure material, m.p. 176°-177° C.

EXAMPLE 3

The product of Example 2 (0.5 g.) was hydrogenated in ethanol (10 ml.) at room temperature and atmospheric pressure using a platinum catalyst (5 mg.). After 4½ hours the mixture was filtered and the filtrate concentrated. The product was recrystallised from a mixture of ether and light petroleum (b.p. 40°-60° C.) to give 2-(2-fluoro-4-biphenylyl)propionic acid, m.p. 112°-113° C.

EXAMPLE 4

DIOP (64.8 mg.) was added to a solution of DTDR (46 mg.) in benzene (9 ml.) under nitrogen and the mixture allowed to stand for 15 minutes. This complex was then added to a mixture, prepared by adding ethanol (16 ml.) followed by (−)-α-methylbenzylamine (24 mg.) in ethanol (2 ml.) to the product of Example 2 (0.5 g.), under hydrogen. The reaction mixture was stirred under hydrogen for 5½ hours at room temperature and then kept under hydrogen overnight. The solution was concentrated under reduced pressure and the residue treated with ether and aqueous 10% potassium carbonate. The ether extract was treated with the potassium carbonate extract, which was then acidified. The oil which separated, solidified and was extracted with ether and the extract dried, filtered, evaporated and the product recrystallised from light petroleum (b.p. 60°-80° C.) to give 2-(2-fluoro-4-biphenylyl)propionic acid, m.p. 101°-103° C., having an optical rotation $[\alpha]_D^{20} + 35.5°$ C. representing 89% of the (+) isomer in the product.

EXAMPLES 5–12

In a similar manner to that described in Example 1 the following compounds were obtained from the appropriate bromo compound. The compounds were purified by recrystallisation from the solvent given in Table I.

TABLE I

| Ex. No. | Compound Obtained | Recrystallisation Solvent | M.P. (°C.) |
|---|---|---|---|
| 5 | 2-Hydroxy-2-(6-methoxy-2-naphthyl)propionic acid | Methanol/water | 167–168 |
| 6 | 2-Hydroxy-2-(3-phenoxyphenyl)propionic acid | " | 99–101 |
| 7 | 2-Hydroxy-2-(4-isobutylphenyl)propionic acid | Petroleum (b.p. 40–60° C.) | 104.5–105.5 |
| 8 | 2-(4-Cyclohexylphenyl)-2-hydroxypropionic acid | Ether/petroleum (b.p. 40–60° C.) | 154–155 |
| 9 | 2-Hydroxy-2-(2-methoxy-4-biphenyl)propionic acid | Toluene | 157.5–158 |
| 10 | 2-Hydroxy-2-(2,2',4'-trifluoro-4-biphenyl)propionic acid | N.C. | 132–134 |
| 11 | 2-(2,2'-Difluoro-4-biphenyl)-2-hydroxypropionic acid | Toluene | 154–155 |
| 12 | 2-[4-(2-Fluorophenoxy)phenyl]-2-hydroxypropionic acid | Toluene | 123–125 |

N.C. = Product not recrystallised.

EXAMPLE 13

In a similar manner to that described in Example 1, the Grignard compound was formed from 3-bromobenzophenone dimethyl ketal and reacted with sodium pyruvate. Crude 2-(3-benzoylphenyl)-2-hydroxy propionic acid was obtained as an oil.

EXAMPLES 14 AND 15

Example 1 was repeated in which the sodium pyruvate was replaced in turn by equivalent amounts of lithium pyruvate and potassium pyruvate.

2-(2-Fluoro-4-biphenylyl)-2-hydroxypropionic acid was obtained in a yield of 32.4% having an m.p. of 163°-166° C. and in a yield of 28% having an m.p. of 161°-163° C. respectively.

EXAMPLES 16–19

In a similar manner to that described in Example 2 the products of Examples 7, 8, 10 and 11 were treated to give the following acrylic acids. The products were recrystallised from the solvent given in the Table II.

TABLE II

| Ex. No. | Product form Ex. No. which is dehydrated | Acrylic acid obtained | Recrystallisation Solvent | M.P. °C. |
|---|---|---|---|---|
| 16 | 7 | 2-(4-isobutylphenyl)acrylic acid | Light petroleum (b.p. 40–60° C.) | 92–94 |
| 17 | 8 | 2-(4-cyclohexylphenyl)acrylic acid | Ether/light petroleum (b.p. 40–60° C.) | 148–149 |
| 18 | 10 | 2-(2,2',4'-trifluoro-4-biphenylyl)acrylic acid | Toluene | 193–194 |
| 19 | 11 | 2-(2,2'-difluoro-4-biphenylyl)acrylic acid | Toluene | 182–183 |

EXAMPLES 20 AND 21

The product of Exampl 9 (2.6 g.) was mixed with p-toluenesulphonic acid (2.63 g.) and benzene (110 ml.) and the mixture heated under reflux for 2 hours. Water, which formed, was removed by means of a Dean and Stark apparatus. The benzene was evaporated and the residue extracted with ether. The extracts were washed with water and extracted with aqueous potassium carbonate (10%). This extract was washed with ether and acidified to give crude 2-(2-methoxy-4-biphenylyl)acrylic acid.

In a similar manner the product of Example 12 gave crude 2-[4-(2-fluorophenoxy)phenyl]acrylic acid.

EXAMPLES 22–27

Example 3 was repeated in which the platinum catalyst was replaced by 10% palladium/charcoal. After recrystallising the product from light petroleum (b.p. 80°–100° C.) 2-(2-fluoro-4-biphenylyl)propionic acid, m.p. 113°–114° C. was obtained.

In a similar manner, the following compounds were obtained by hydrogenating the acrylic acids from Examples 16 and 18–21. The products were recrystallised from the solvent given in the Table III.

TABLE III

| Ex. No. | Product from Ex. No. which is hydrogenated | Propionic acid obtained | Recrystallisation Solvent | M.P. °C. |
|---|---|---|---|---|
| 23 | 16 | 2-(4-isobutylphenyl)propionic acid | Light Petroleum (b.p. 60–80° C.) | 72–76 |
| 24 | 18 | 2-(2,2',4'-trifluoro-4-biphenylyl) propionic acid | Light Petroleum (b.p. 60–80° C.) | 106–107 |
| 25 | 19 | 2-(2,2'-difluoro-4-biphenylyl)propionic acid | None | 117 |
| 26 | 20 | 2-(2-methoxy-4-biphenyl)propionic acid | None | 119–120 |
| 27 | 21 | 2-[4-(2-fluorophenoxy)phenyl]propionic acid | Light Petroleum (b.p. 100–120° C.) | 100–101 |

EXAMPLES 28–30

Example 1 was repeated in which the sodium pyruvate was replaced by an equivalent amount of the following amides. After the reaction with the Grignard reagent by heating under reflux for 60 minutes the product was isolated by addition of water (200 ml.) followed by extraction with ether. The ether extract was washed with water, dried and concentrated under reduced pressure. Light petroleum (b.p. 62°–8° C.) was added and the solution concentrated by evaporation under reduced pressure when the product crystallised and was collected.

The details of the products are given in the Table IV.

TABLE IV

| Ex. No. | Starting Amide | Product | Yield (%) | M.P. (°C.) |
|---|---|---|---|---|
| 28 | CH₃COCONMe₂ | 2-(2-fluoro-4-biphenylyl)-2-hydroxy-N,N-dimethylpropionamide | 37 | 135–137 |
| 29 | CH₃COCONEt₂ | N,N-diethyl-2-(2-fluoro-4-biphenylyl)-2-hydroxy-propionamide | 64 | 111–112 |
| 30 |  | 2-(2-fluoro-4-biphenylyl)-2-hydroxy-N,N-3-oxapentamethylenepropionamide | 42 | 155–156 |

The N,N-3-oxapentamethylene pyruvic acid amide was prepared by heating hydroxymaleic anhydride-pyridine complex with morpholine in toluene to 100° C. until evolution of carbon dioxide ceased. The product was recovered by distillation, b.p. 126°–8° C./8 mm.

EXAMPLES 31–33

The products from Examples 28–30 were treated in a similar manner to that described in Example 2. The product of Example 28 gave 2-(2-fluoro-4-biphenylyl)-N,N-dimethyl acrylamide, obtained as an oil; the product of Example 29 gave N,N-diethyl-2-(2-fluoro-4-biphenylyl)acrylamide, obtained as an oil, and the product of Example 30 gave 2-(2-fluoro-4-biphenylyl)-N,N-3-oxapentamethyleneacrylamide, obtained as a white solid, m.p. 102° C., after recrystallising from light petroleum (b.p. 62°–68° C.).

EXAMPLES 34–36

The products of Examples 31–33 were hydrogenated in a similar manner to that described in Example 22. The product of Example 31 gave 2-(2-fluoro-4-biphenylyl)-N,N-dimethyl propionamide, obtained as a white solid, m.p. 67°–69° C. after recrystallising from light petroleum (b.p. 62°–68° C.); the product of Example 32 gave N,N-diethyl-2-(2-fluoro-4-biphenylyl)propionamide, obtained as an oil, and the product of Example 33 gave 2-(2-fluoro-4-biphenylyl-N,N-3-oxapentamethylenepropionamide, obtained as a white solid m.p. 96°–98° C. after recrystallising from light petroleum (b.p. 62°–68° C.)

EXAMPLE 37

The products from Example 34 were heated under reflux for two days with a mixture of glacial acetic acid, concentrated sulphuric acid and water (volume ratio 10:1:1.5). The reaction mixture was added to water, extracted with ether and then aqueous potassium carbonate (10%) and this extract acidified and the precipitate collected to give 2-(2-fluoro-4-biphenylyl)propionic acid. The products of Examples 35 and 36 also gave the same product when treated in a similar manner.

EXAMPLE 38

Example 4 was repeated in which the DTDR was replaced by an equivalent amount of DODDR and the DIOP was replaced by an equivalent amount of (−)-2,3-bis(diphenylphosphinomethyl)-1,4-dioxaspiro[4,4-]nonane, prepared by: (a) reacting L-(+)-diethyl tartrate with cyclopentanone in benzene in the presence of p-toluenesulphonic acid to give diethyl 1,4-dioxaspiro[4,4]nonan-2,3-dicarboxylate, b.p. 154°–158° C./6.0 mm., (b) reducing this with lithium aluminium hydride to give (−)-2,3-O-cyclopentylidene-L-threitol, b.p. 124°–130° C./0.2 mm., (c) converting this to (−)-1,4-ditosyl-2,3-O-cyclopentylidene-L-threitol m.p. 109°–115.5° C. by reaction with p-toluenesulphonyl chloride in pyridine and (d) treating with potassium and diphenylphosphine in tetrahydrofuran to give the desired compound m.p. 93°–95° C.

The 2-(2-fluoro-4-biphenylyl)propionic acid obtained had an m.p. 102°–105° C. and $[\alpha]_D^{20}+36.0°$, representing 90% of the (+) isomer in the product.

EXAMPLES 39–40

Example 4 was repeated in which the α-methylbenzylamine was replaced with in turn di-n-propylamine and isopropylamine. The resulting 2-(2-fluoro-4-biphenylyl)propionic acid had respectively m.p. 101°–104.5° C. and $[\alpha]_D^{24}+37.0°$, representing 91% of the (+) isomer in the product and m.p. 102°–104° C. and $[\alpha]_D^{29}+36.0$, representing 90% of the (+) isomer in the product.

EXAMPLE 41

Nitrogen was bubbled through a mixture of DODDR (14 mg.), DIOP (30 mg.) and isopropanol (5 ml.) which had previously been degassed with nitrogen for ½ hour and the flask was evacuated and then flushed with hydrogen 6 times. The mixture was stirred under hydrogen for 20 minutes and then 2-(2-fluoro-4-biphenylyl)acrylic acid (0.5 g.) from Example 2 and (−)-α-methylbenzylamine (22 mg.) in isopropanol (20 ml.), which had been degassed with nitrogen, was added with a syringe through a rubber cap covering the flask. The mixture was stirred for a further 20 hours until the requisite amount of hydrogen had been taken up. The solution was concentrated under reduced pressure and the residue isolated in ether and the ether solution extracted with aqueous potassium carbonate. The extract was washed with ether and acidified. The precipitate was extracted with ether and the extract washed with water, dried and evaporated to dryness. The residue was dissolved in hot light petroleum (b.p. 60°–80° C.). This solution was treated with charcoal, filtered and rapidly cooled to room temperature by placing the flask containing it under cold running water. At the same time it was seeded with almost pure (+) product and the flask was scratched with a glass rod. The resultant, rapidly crystallised product, after separation and drying had an $[\alpha]_D^{20}+43.2°$, representing 98% of the (+) isomer in the product, and m.p. 105°–107° C.

EXAMPLE 42

The product of Example 1 (5.2 g.; 0.02 mole) in warm industrial methylated spirits (50 ml.) was treated with (−)-α-methylbenzylamine (2.4 g.; 0.02 mole) in industrial methylated spirits (2.0 ml.). The solution was allowed to stand at 25° C. for two hours and the colourless crystals which separated were collected. This solid was recrystallised twice more from industrial methylated spirits. The product was collected, acidified with dilute sulphuric acid and the free acid extracted into ether. The extract was washed with water, dried and evaporated to dryness to give (+)-2-(2-fluoro-4-biphenylyl)-2-hydroxypropionic acid having $[\alpha]_D^{20}+40.0°$ and m.p. 150°–152° C.

The mother liquors from the above recrystallisations were evaporated to dryness and the residue was acidified with dilute sulphuric acid. The acid was extracted with ether, the extract washed with water, dried, evaporated to dryness and the residue treated with an equivalent amount of (+)-α-methylbenzylamine in industrial methylated spirits. The product was allowed to crystallise and recrystallised from industrial methylated spirits.

The product was acidified and the free acid extracted and purified as described above to give (−)-2-(2-fluoro-4-biphenylyl)-2-hydroxypropionic acid, having $[\alpha]_D^{20}-39.5°$ and m.p. 149°–151° C.

EXAMPLE 43

The product from Example 1 (5 g.) was added to acetic anhydride (50 ml.) and the mixture heated on a steam bath for 2 hours after the acid had all dissolved. The mixture was then cooled and poured into water (200 ml.). The aqueous mixture was allowed to stand for 2 hours and the product collected recrystallised from a mixture of ether and light petroleum (b.p. 62°–68° C.) gave 2-acetoxy-2-(2-fluoro-4-biphenylyl)propionic acid, m.p. 141°–142° C.

EXAMPLES 44–45

(+)-2-(2-Fluoro-4-biphenylyl)-2-hydroxypropionic acid (1 g.) from Example 42 was added to acetic anhydride (10 g.) and the mixture stirred overnight at room temperature. The mixture was added to water (40 ml.) and allowed to stand for two hours. The product was collected and recrystallised from a mixture of ether and light petroleum (b.p. 62°–68° C.) to give (−)-2-acetoxy-2-(2-fluoro-4-biphenylyl)propionic acid, m.p. 125°–127° C. and $[\alpha]_D^{20}-33.0°$.

In a similar manner, starting from (−)-2-(2-fluoro-4-biphenylyl)-2-hydroxypropionic acid, there was obtained (30  )-2-acetoxy-2-(2-fluoro-4-biphenylyl)propionic acid, m.p. 125°–127° C. and $[\alpha]_D^{20}+32.0°$.

EXAMPLE 46

The product from Example 44 was hydrogenated at 25° C. in glacial acetic acid using a 10% palladium/charcoal catalyst, for 17 hours. The filtrate from catalyst was evaporated and applied to preparative thin layer chromatography plates and eluted with an ether/petroleum (b.p. 62°–68° C.) mixture (5%: 95%) whereby 2-(2-fluoro-4-biphenylyl)propionic acid, $[\alpha]_D^{20}-29.5°$, was recovered. This represents 82% of the (−)-isomer in the product.

The products from Examples 43 and 45 were similarly hydrogenated, at 60° C. and 50° C. respectively, but were not subjected to thin layer chromatography. In both cases 2-(2-fluoro-4-biphenylyl)propionic was shown to have been produced in major amount by G.L.C. The reaction mixture obtained by hydrogenating the (−)-2-acetoxy-2-(2-fluoro-4-biphenylyl)propionic acid from Example 45 had $[\alpha]_D^{20}+34.0°$.

EXAMPLE 47

The product of Example I (5 g.) was heated under reflux with methanol (50 ml.) and concentrated sulphuric acid (1 ml.) for 4 hours. The product was poured into water, extracted with ether, the ether extracts dried and evaporated to give methyl 2-(2-fluoro-4-biphenylyl)-2-hydroxypropionate, m.p. 59°–61° C. This ester (1 g.) was dissolved in thionyl chloride (5 ml.) and heated on a water bath at 50° C. for two hours. Thionyl chloride was removed and the product was applied to preparative thin layer chromatography plates, eluted with an ether/petroleum (b.p. 62°–68° C.) mixture (5% 95%) and methyl 2-chloro-2-(2-fluoro-4-biphenylyl)propionate recovered. This was dissolved in ethyl acetate (5 ml.) and hydrogenated at room temperature using a 10% palladium/charcoal catalyst (73 mg.) for 16 hours. The solution was filtered and evaporated to give methyl 2-(2-fluoro-4-biphenylyl)propionate, whose structure was confirmed by n.m.r. This was hydrolysed by heating under reflux with aqueous ethanolic potassium hydroxide. The solution was acidified, extracted with ether and then aqueous potassium carbonate (10%) and this extract acidified and the precipitate collected to give 2-(2-fluoro-4-biphenylyl)propionic acid (m.p t. 105°–106° C.).

COMPARATIVE EXAMPLES

Example 1 was repeated in which the sodium pyruvate was replaced by an equivalent amount of pyruvic acid. The yield of 2-(2-fluoro-4-biphenylyl)-2-hydroxypropionic acid was only 18% and had a melting point of 163°–165° C.

In a similar manner Example 1 was repeated in which the sodium pyruvate was replaced by an equivalent amount of ethyl pyruvate. An oil was obtained containing 21% of ethyl 2-(2-fluoro-4-biphenylyl)-2-hydroxypropionate representing a yield of only 14.5% of this ester.

What we claim is:
1. 2-(2-Fluoro-4-biphenylyl)-2-hydroxypropionic acid and its enantiomers.